United States Patent
Fleury et al.

(10) Patent No.: US 6,878,136 B2
(45) Date of Patent: Apr. 12, 2005

(54) HUBER NEEDLE WITH ANTI-REBOUND SAFETY MECHANISM

(75) Inventors: Michael T. Fleury, Portage, WI (US); Fergie F. Ferguson, Brea, CA (US); Dongchul D. Hyun, Brea, CA (US)

(73) Assignee: Medical Product Specialists, Brea, CA (US)

(*) Notice: Subject to any disclaimer, the term of this patent is extended or adjusted under 35 U.S.C. 154(b) by 81 days.

(21) Appl. No.: 10/350,765

(22) Filed: Jan. 24, 2003

(65) Prior Publication Data

US 2003/0163097 A1 Aug. 28, 2003

Related U.S. Application Data

(60) Provisional application No. 60/360,406, filed on Feb. 28, 2002.

(51) Int. Cl.[7] .................................. A61M 5/32
(52) U.S. Cl. .................. 604/272; 604/174; 604/198; 128/919
(58) Field of Search ............................ 604/93.01, 110, 604/116, 117, 162, 164.04, 164.07, 164.08, 165.01, 165.02, 165.03, 165.04, 174, 177, 192, 197, 198, 263, 264, 272; 128/919

(56) References Cited

U.S. PATENT DOCUMENTS

| | | |
|---|---|---|
| 3,924,617 A | 12/1975 | Ferro |
| 4,411,657 A | 10/1983 | Galindo |
| 4,413,993 A | 11/1983 | Guttman |
| 4,675,006 A | 6/1987 | Hrushesky |
| 4,753,641 A | 6/1988 | Vaslow |
| 4,755,173 A | 7/1988 | Konopka |
| 4,772,272 A | 9/1988 | McFarland |
| 4,795,432 A | 1/1989 | Karczmer |
| 4,804,371 A | 2/1989 | Vaillancourt |
| 4,906,236 A | 3/1990 | Alberts et al. |

(Continued)

*Primary Examiner*—Nicholas D. Lucchesi
*Assistant Examiner*—Mark K. Han
(74) *Attorney, Agent, or Firm*—Stetina Brunda Garred & Brucker

(57) ABSTRACT

A safety needle device for protecting a user against inadvertent needle-stick injury. This needle device includes a needle housing having a distal housing opening. An arcuate groove extends within the needle housing terminating adjacent the distal housing opening. A needle is disposed within the arcuate groove having a distal needle portion extending away from the needle housing through the distal housing opening. An elongate sheath assembly surrounds the needle within the groove. A biasing member is disposed within the needle housing and is configured to move the sheath assembly throughout the length of the arcuate groove and through the distal housing opening. The sheath assembly then completely enclose the distal needle portion.

2 Claims, 7 Drawing Sheets

U.S. PATENT DOCUMENTS

| | | | | |
|---|---|---|---|---|
| 4,929,237 A | | 5/1990 | Medway | |
| 4,990,135 A | | 2/1991 | Truesdale, Jr. | |
| 5,015,240 A | | 5/1991 | Soproni et al. | |
| 5,092,851 A | * | 3/1992 | Ragner | 604/192 |
| RE34,045 E | | 8/1992 | McFarland | |
| 5,135,504 A | | 8/1992 | McLees | |
| 5,176,650 A | | 1/1993 | Haining | |
| 5,176,656 A | | 1/1993 | Bayless | |
| 5,254,106 A | | 10/1993 | Feaster | |
| 5,267,974 A | | 12/1993 | Lambert | |
| 5,279,582 A | | 1/1994 | Davison et al. | |
| 5,318,547 A | * | 6/1994 | Altschuler | 604/198 |
| 5,328,482 A | | 7/1994 | Sircom et al. | |
| 5,364,362 A | | 11/1994 | Schulz | |
| 5,403,283 A | | 4/1995 | Luther | |
| D365,630 S | | 12/1995 | Sullivan | |
| 5,478,238 A | | 12/1995 | Gourton et al. | |
| 5,520,654 A | | 5/1996 | Wahlberg | |
| 5,591,138 A | * | 1/1997 | Vaillancourt | 604/263 |
| 5,611,781 A | | 3/1997 | Sircom et al. | |
| 5,662,619 A | | 9/1997 | Zarate | |
| 5,702,369 A | | 12/1997 | Mercereau | |
| 5,713,874 A | | 2/1998 | Ferber | |
| 5,725,503 A | | 3/1998 | Arnett | |
| 5,746,215 A | | 5/1998 | Manjarrez | |
| 5,755,699 A | | 5/1998 | Blecher et al. | |
| 5,795,336 A | | 8/1998 | Romano et al. | |
| 5,817,058 A | | 10/1998 | Shaw | |
| 5,846,227 A | | 12/1998 | Osterlind | |
| 5,848,996 A | | 12/1998 | Eldor | |
| 5,851,196 A | | 12/1998 | Arnett | |
| 5,879,330 A | | 3/1999 | Bell | |
| 5,891,098 A | | 4/1999 | Huang | |
| 5,893,845 A | | 4/1999 | Newby et al. | |
| 5,951,512 A | | 9/1999 | Dalton | |
| 5,951,522 A | | 9/1999 | Rosato et al. | |
| 5,964,739 A | | 10/1999 | Champ | |
| 5,997,504 A | | 12/1999 | Bell | |
| 6,120,492 A | | 9/2000 | Finch et al. | |
| 6,165,157 A | | 12/2000 | Dillon et al. | |
| 6,186,179 B1 | | 2/2001 | Hill | |
| 6,210,371 B1 | | 4/2001 | Shaw | |
| 6,238,375 B1 | | 5/2001 | Powell | |
| 6,241,710 B1 | | 6/2001 | VanTassel et al. | |
| 6,261,259 B1 | | 7/2001 | Bell | |
| 6,261,264 B1 | | 7/2001 | Tamaro | |
| 6,261,272 B1 | | 7/2001 | Gross et al. | |
| 6,280,420 B1 | | 8/2001 | Ferguson et al. | |
| 6,280,424 B1 | | 8/2001 | Chang et al. | |
| 6,290,683 B1 | | 9/2001 | Erez et al. | |
| 6,322,537 B1 | | 11/2001 | Chang | |
| 6,346,096 B1 | | 2/2002 | Ranford et al. | |
| 6,355,021 B1 | | 3/2002 | Nielsen et al. | |
| 6,659,983 B2 | * | 12/2003 | Crawford et al. | 604/192 |
| 2001/0039401 A1 | | 11/2001 | Ferguson et al. | |
| 2002/0010434 A1 | | 1/2002 | Larsen et al. | |
| 2002/0072716 A1 | | 6/2002 | Barrus et al. | |

* cited by examiner

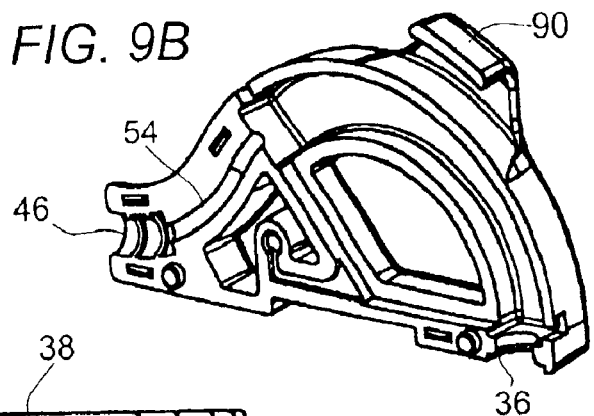
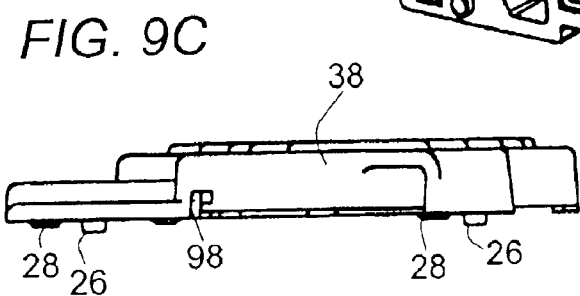
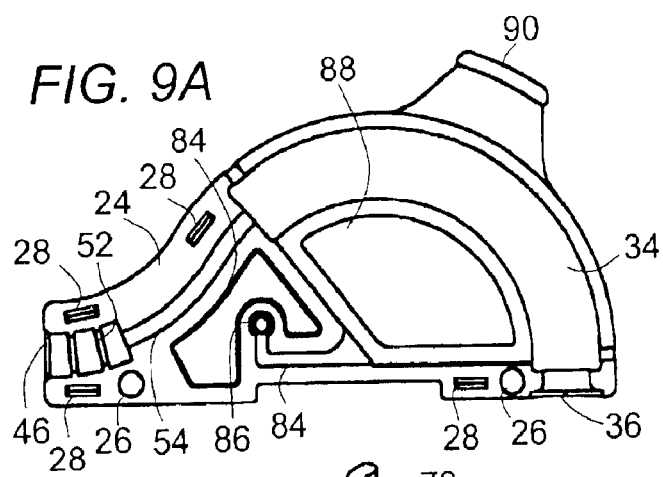
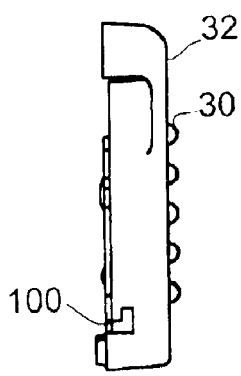
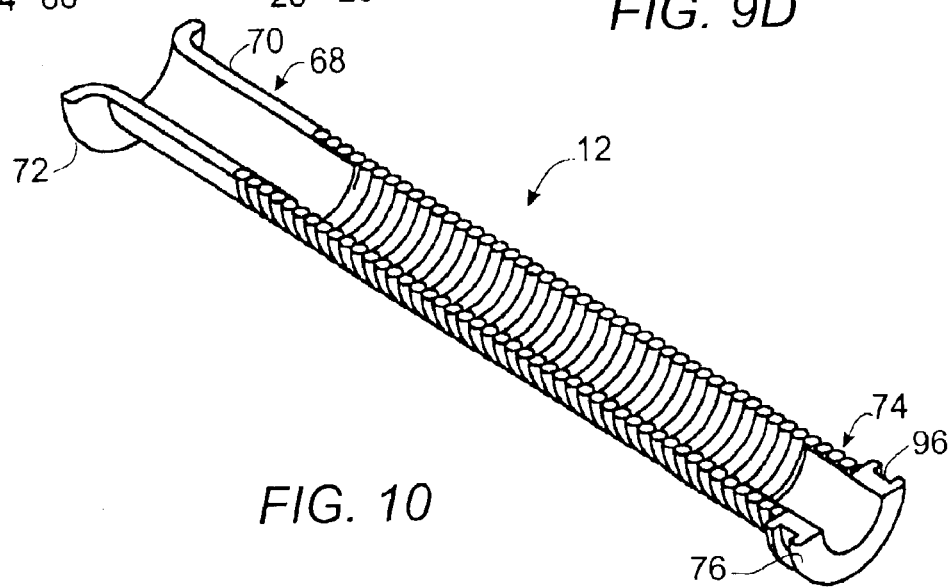

HUBER NEEDLE WITH ANTI-REBOUND SAFETY MECHANISM

CROSS-REFERENCE TO RELATED APPLICATIONS

This application claims the benefit of U.S. Provisional Application No. 60/360,406 entitled "HUBER NEEDLE WITH ANTI-REBOUND MECHANISM" filed Feb. 28, 2002, the entirety of the disclosure of which is expressly incorporated herein by reference.

STATEMENT RE: FEDERALLY SPONSORED RESEARCH/DEVELOPMENT (Not Applicable)

BACKGROUND OF THE INVENTION

The present invention relates generally to medical needle devices, and more particularly to an improved safety needle device featuring a sheath assembly which is designed to be outwardly deployable relative to the exposed portion of an affixed needle and enclose the same therewithin to protect its user against inadvertent needle-stick injuries.

Needle-stick injuries are common and are of great concern in today's health-care industry. A vast majority of these injuries occur while withdrawing conventional Huber needles from implanted IV ports after administering medicants such as antibiotics or chemotherapy.

More specifically, a great deal of force is required during Huber needle withdrawal to overcome the resistance of the port's septum. Since a non-dominant hand is typically used in this process to secure the implanted port, it often becomes stuck on the rebound of the Huber needle.

Because a Huber needle is utilized for venous access, such needle-stick injury as described above presents a high risk for pathogen transmission. An exposed and/or injured health-care worker must be tested for various blood-borne pathogens such as hepatitis B, hepatitis C and HIV.

Such testing is usually repeated to ensure that the exposed and/or injured health-care worker is not infected of those pathogens. As a further precaution, boosting of immunity may simultaneously take place as an additional insurance of safety.

In order to alleviate the dangers associated with needle-stick injuries, some health-care workers have fashioned home-made guards to protect their non-dominant hands. However, these home-made guards are not user-friendly as the health-care workers must make the conscious choice to wear them every time an injection is made.

The health-care workers may sometimes neglect to put them on because they are either inconvenient to use, interfere with the process of administering the Huber needle or the health-care workers may just simply forget to wear them. All of these factors contribute to negating the guards' effectiveness to protect the health-care workers against the dangers of needle-stick injuries.

In view of the above-described shortcomings of conventional needle guards, there exists a need in the art for a safety needle guard which can protect health-care workers against the dangers of needle-stick injuries in a convenient and user-friendly manner. More specifically, there exists a need for a safety needle guard which can be automatically implemented in a user passive manner during the needle injection process so as to consistently protect the health-care workers against the dangers of needle-stick injuries.

BRIEF SUMMARY OF THE INVENTION

The present invention specifically addresses and alleviates the above-referenced deficiencies associated with the use of the Huber needle guards of the prior art. More particularly, the present invention is an improved safety needle device featuring a sheath assembly which is outwardly deployable relative to the exposed portion of its affixed needle. By such deployment, a physical barrier can be placed around the needle by the sheath assembly to protect a user from being inadvertently stuck by the needle, thus preventing needle-stick injuries and all the risks that are associated with them. Although this sheath assembly is intended to be used for Huber needle applications, it is specifically recognized herein that such sheath assembly may be used in conjunction with other types of conventional needle applications as well.

In accordance with a preferred embodiment of the present invention, there is provided an active safety needle device for protecting its user against a needle-stick injury. The safety needle device of the present invention first features a needle housing comprised of two substantially identical housing halves engaged to each other about their respective inner housing faces. Although such housing halves may be engaged in any manner or fashion, it is preferred that such engagement occurs through ultrasonic welding. Moreover, each of the two housing halves are preferably fabricated from a plastic material such as through the process of plastic injection molding.

The needle housing includes an internal groove which is elongated therewithin and communicates with its distal opening. This groove is preferably elongated in a manner as to substantially correspond to (i.e., be complementary to) parallel the general arcuate curvature of the needle housing's upper surface. In this respect, the internal groove defines a bend radius which is complementary in shape to the upper housing surface.

In the preferred embodiment of the present invention, the needle housing further includes a needle, of which its intermediate portion is disposed within the elongated groove. In this regard, that portion of the needle is formed in an arcuate configuration to match the bend radius of the groove so it can be accommodated therewithin. The needle utilized with the present needle device is preferably a stainless steel Huber needle having a non-coring distal needle point.

The needle defines a proximal needle portion which becomes exposed outside of the needle housing by extending through the needle housing's proximal opening. Flexible infusion tubing preferably made from silicone rubber and/or polyvinyl chloride or polyethylene surrounds this exposed proximal portion of the needle and connects to the needle housing through its proximal opening. The infusion tube or tubing can be maintained in this position by the engagement of the two housing halves which compress on the tubing.

A distal portion of the needle is defined generally opposite to the proximal needle portion. The needle portion is retained outside of the needle housing as it is extended downward through the distal housing opening. The distal needle portion forms a needle point at its exposed end which is used for penetrating the patient's skin and accessing the implanted port.

In the preferred embodiment, the needle housing has a lower housing surface that defines a lower housing recess. This recess is primarily intended for accommodating a hold-down platform. The hold-down platform may be engaged within the recess through a variety attachment procedures such as adhesive or fastener. By providing platform strips which radially extend outward from such location of engagement, the hold-down platform may be placed near the injection point and be used for securing the safety needle device upon the patient by means of taping over the platform strips and the patient's skin. Preferably, the hold-down platform has a generally circular or rectangular configuration, and is fabricated from either a rubber or plastic material.

In accordance with a preferred embodiment of the present invention, an elongate sheath assembly is provided within the needle housing. More specifically, this sheath assembly is situated within the groove when disposed in a retracted position surrounding the intermediate portion of the needle. The sheath assembly has an axial length that is substantially identical to that of the elongated groove. Although the sheath assembly may be formed from various materials, it is preferably formed as an elongate wound stainless steel wire tube and/or semi-rigid polymer such as polyethylene or Teflon.

The sheath assembly of the preferred embodiment defines a distal sheath end. Attached to this end is a distal tip component which preferably comprises a transparent plastic tip. The tip component can be either insert molded or adhered to the distal sheath end. The distal tip component forms a distal tip having a diameter which is generally greater than that of the groove but substantially equal to or less than the diameter of the distal housing opening.

The sheath assembly further defines a proximal sheath end generally opposite to the distal sheath end. Attached to the proximal sheath end is a proximal tip component having a diameter which is generally greater than the diameter of the groove's distal opening. As will be discussed more fully below, such configuration allows the sheath assembly to stop once reaching the fully extended position, that is, the distal tip component being advanced over and beyond the distal needle point while enclosing the distal needle portion with the sheath assembly. Although other types of tip components may be contemplated, the proximal tip component utilized with the present invention is preferably formed as a stainless steel or plastic ferrule.

In the preferred embodiment of the present invention, a biasing member is provided within the needle housing. This biasing member is used for actively moving the sheath assembly along the groove between the retracted and extended positions. The biasing member is connected between the proximal tip component and a knob member disposed on the exterior of the needle housing.

The knob member allows the user to control the movement of the sheath assembly along the elongated groove. This is possible due to the mechanical connections with the proximal tip component of the sheath assembly and the biasing member. Because the preferred biasing member comprises a torsional biasing member which is configured to naturally urge the sheath assembly towards the extended position, the user may utilize the knob member to control the sheath assembly when moving along that direction.

In the preferred embodiment, the biasing member comprises either a torsional arm or torsional spring. However, other types of biasing members are contemplated as they may also achieve the ultimate objective of actively deploying the sheath assembly outwardly with respect to the distal needle portion.

In operation, the present safety needle device protects the user from inadvertent needle stick during withdrawal of the needle from the patient. More specifically, the distal needle point is first injected into a designated skin area of the patient to access the implanted IV port. By such penetration, various tasks such as delivering fluids and medications, drawing blood for diagnostic testing and/or infusing blood products may be conducted. Optionally, the needle device can be secured in place by taping its platform strips to the patient's surrounding skin area.

After performing any one of the tasks as described above, the needle is withdrawn from the patient. While withdrawing the needle, the sheath assembly is deployed outwardly from within the needle device relative to the distal needle portion resulting in the distal needle portion being completely enclosed and/or surrounded by the outwardly deployed sheath assembly. Such process can be facilitated by using the externally located knob member which allows the user to control the outward deployment of the sheath assembly.

The needle device is then ready for proper disposal in a Sharps container or other container designated for used medical devices.

BRIEF DESCRIPTION OF THE DRAWINGS

These as well as other features of the present invention will become more apparent upon reference to the drawings wherein:

FIG. 9a is a side view of one housing half which is used to form the needle housing of FIG. 1 when engaged with the other housing half;

FIG. 9b is a perspective view of the housing half of FIG. 9a illustrating pegs formed about an inner housing face thereof;

FIG. 9c is a top view of the housing half of FIG. 9a illustrating its upper housing surface forming a proximal notch;

FIG. 9d is a rear view of the housing half of FIG. 9a illustrating its side housing surface forming finger-graspable projections;

FIG. 10 is a perspective cross-sectional view of the sheath assembly of FIGS. 2 and 3 illustrating its proximal and distal tip components;

DETAILED DESCRIPTION OF THE INVENTION

Figure 1:
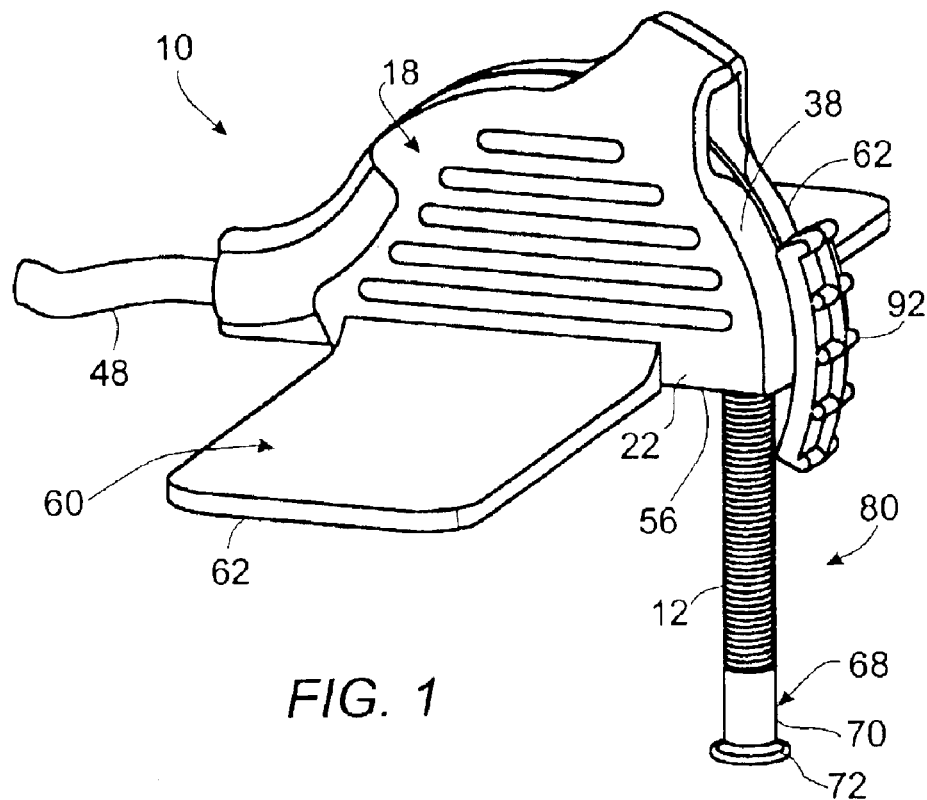
FIG. 1 is a perspective view of a safety needle device constructed in accordance with a preferred embodiment of the present invention and illustrating its needle housing and having generally rectangular platform strips radially extending outward therefrom.

Referring now to the drawings wherein the showings are for purposes of illustrating preferred embodiments of the present invention only, and not for purposes of limiting the same, FIG. 1 illustrates an active safety needle device 10 constructed in accordance with a preferred embodiment of the present invention. As indicated above, the present safety needle device 10 features a sheath assembly 12 which is outwardly deployable with respect to the distal needle portion 14, that is, the exposed portion of its affixed needle 16 which is used to access an IV port implanted underneath a patient's designated skin area (not shown).

As will be soon discussed, such active deployment of the sheath assembly 12 provides a tangible physical barrier around the distal needle portion 14 to protect a user from being inadvertently stuck by the needle 16, thereby preventing needle-stick injuries and all the risks associated therewith. Although the sheath assembly 12 is preferably used for Huber needle applications, it is expressly contemplated herein that such sheath assembly 12 may be used for other types of conventional needle applications as well.

Referring more particularly to FIGS. 1 and 9a–9c, the safety needle device 10 includes a needle housing 18. Although this needle housing 18 may be formed from a unitary construction, it is preferably constructed from two substantially identical housing halves 20, 22 which are assembled to each other about their respective inner housing faces 24. The first housing half 20 includes at least one peg 26 that can be retained within at least one corresponding aperture (not shown) provided on the second housing half 22. The permanent engagement between the two housing halves 20, 22 is preferably accomplished with adhesive or ultrasonic welding or snap fit engagement.

The two substantially identical housing halves 20, 22 may be fabricated from any rigid material. However, the material of choice is a polymer (i.e., plastic). In this respect, the manufacture of each housing half 20 or 22 may be greatly expedited through utilizing the process of plastic injection molding techniques.

Figure 11:
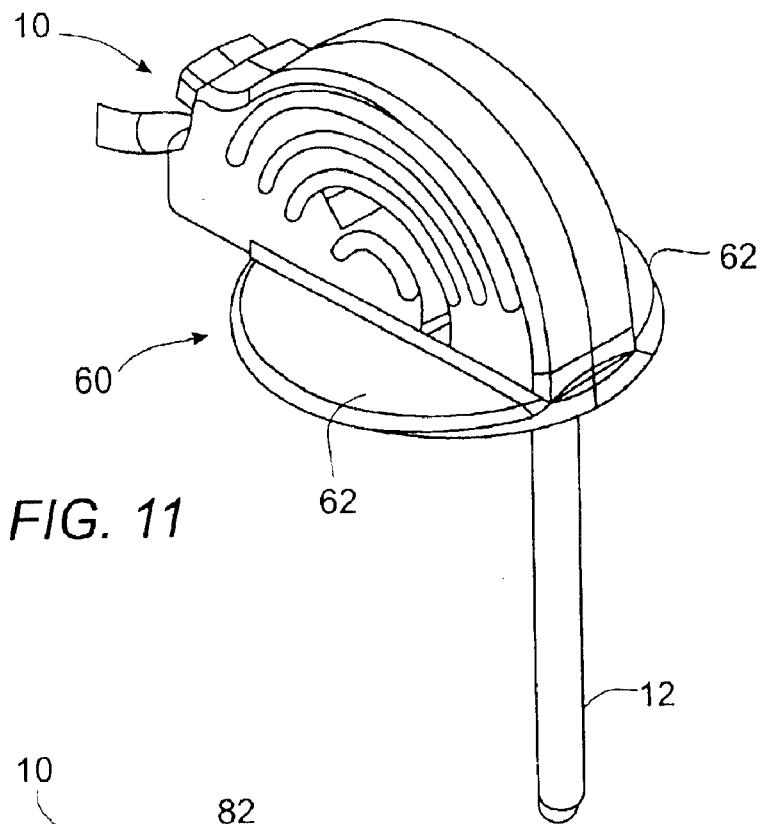
FIG. 11 is a perspective view of the safety needle device of FIG. 1 and illustrating its needle housing which uses generally half-circular platform strips as an alternative to the generally rectangular platform strips.
Figure 12:
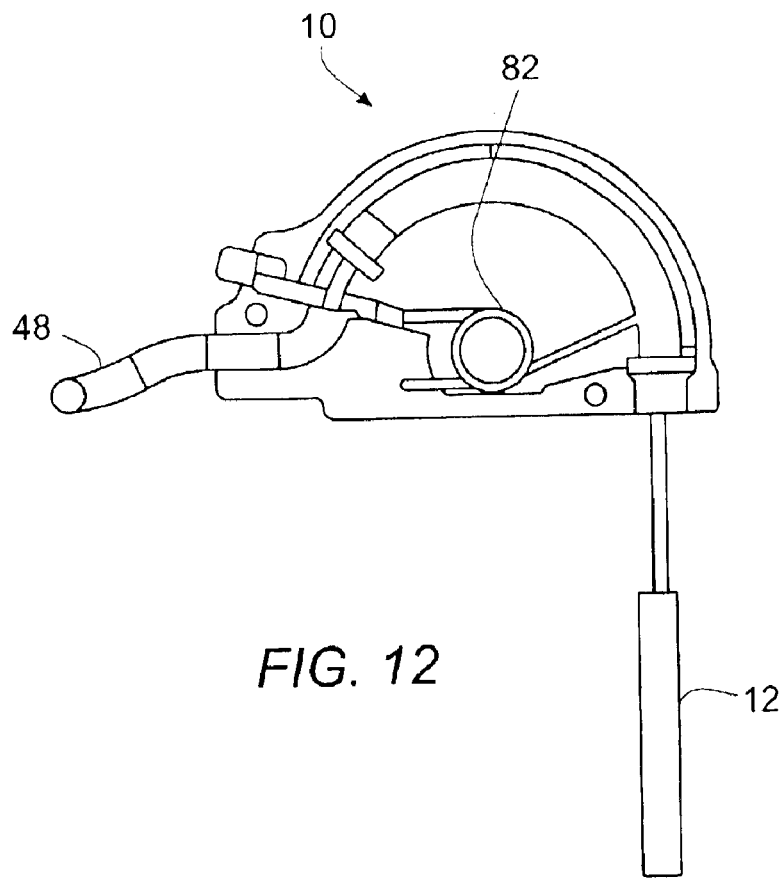
FIG. 12 is a side cross-sectional view of the safety needle device of FIG. 11 illustrating the use of a torsional spring as an alternative to the torsional arm.

Referring now to FIGS. 9d and 11, the exterior of the needle housing 18 preferably includes plural projections 30 to ease in the handling of the present safety needle device 10. These projections 30 may be formed on one or both sides 32 of the needle housing 18. As can be seen from the specified figures, the finger-graspable projections 30 may be provided as a group of linearly configured projections (as shown in FIG. 9d) or arcuately configured projections (as shown in FIG. 11).

Figure 2:
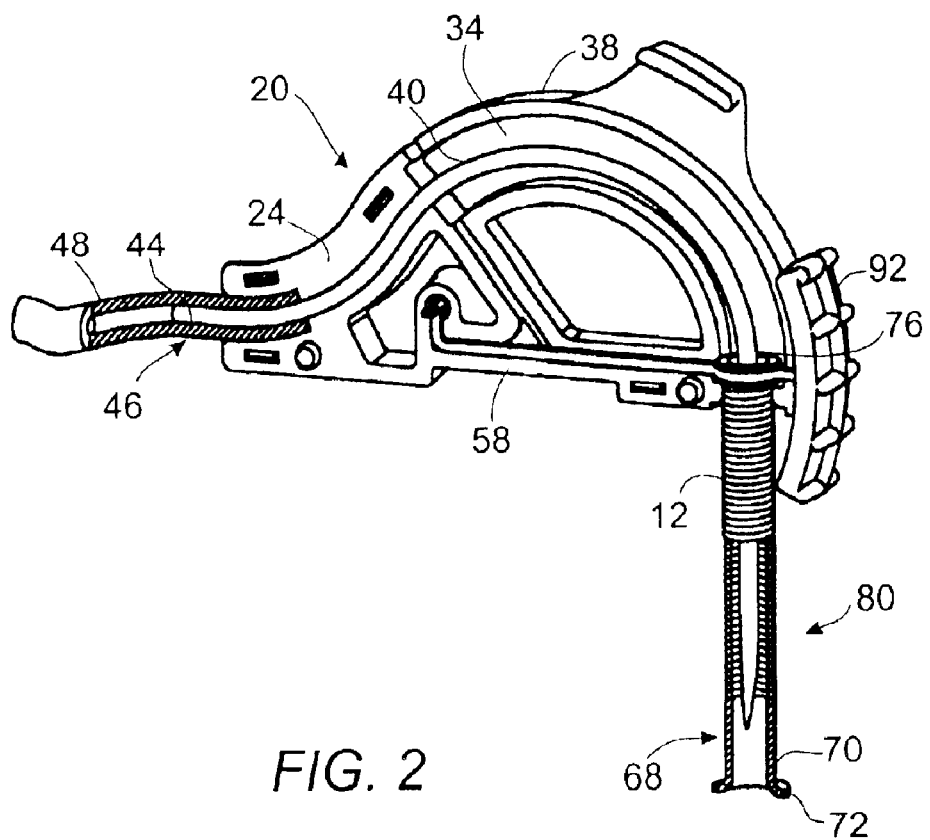
FIG. 2 is a perspective cross-sectional view of the safety needle device of FIG. 1 and illustrating the manner in which a sheath assembly is extended from within its needle housing.
Figure 4:
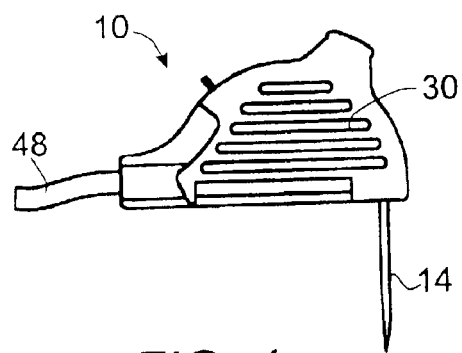
FIG. 4 is a side view of the safety needle device of FIG. 1 and illustrating a needle's exposed distal portion which extends downward out of its needle housing.
Figure 6A:
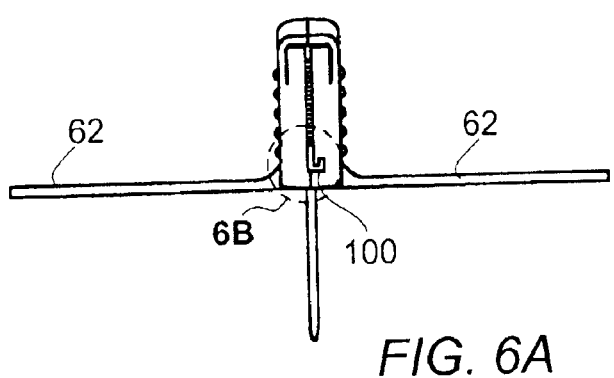
FIG. 6a is a front view of the safety needle device of FIG. 1 illustrating a needle's distal portion which is disposed generally perpendicular to the radially extending platform strips.

As shown in FIGS. 2 and 4, the needle housing 18 includes an internal arcuate groove 34 which initiates intermediate the housing and extends to a distal opening 36 of the needle housing 18. Preferably, the groove 34 is formed in a generally complementary configuration to the general arcuate curvature of the needle housing's upper surface 38. As such, the internal groove 34 has a bend radius which closely simulates the bend radius of the upper housing surface 38.

The needle housing also contains a needle 16, of which an intermediate portion 40 thereof is disposed within the elongated groove 34. The intermediate needle portion 40 is sufficiently formed (i.e., bent to closely match the bend radius of the internal groove 34 so as to be accommodatingly disposed therewithin). The needle 16 preferably used with the present safety needle device 10 comprises a stainless steel Huber needle. However, other types of needles such as a conventional hypodermic syringe needle may be workable with the present safety needle device 10. Preferably, the needle 16 has a needle point 42 which is non-coring but use of the coring needle point may be contemplated. Of course, the needle point 42 is intended for penetrating a designated area of the patient's skin and accessing an IV port implanted underneath.

Figure 3:
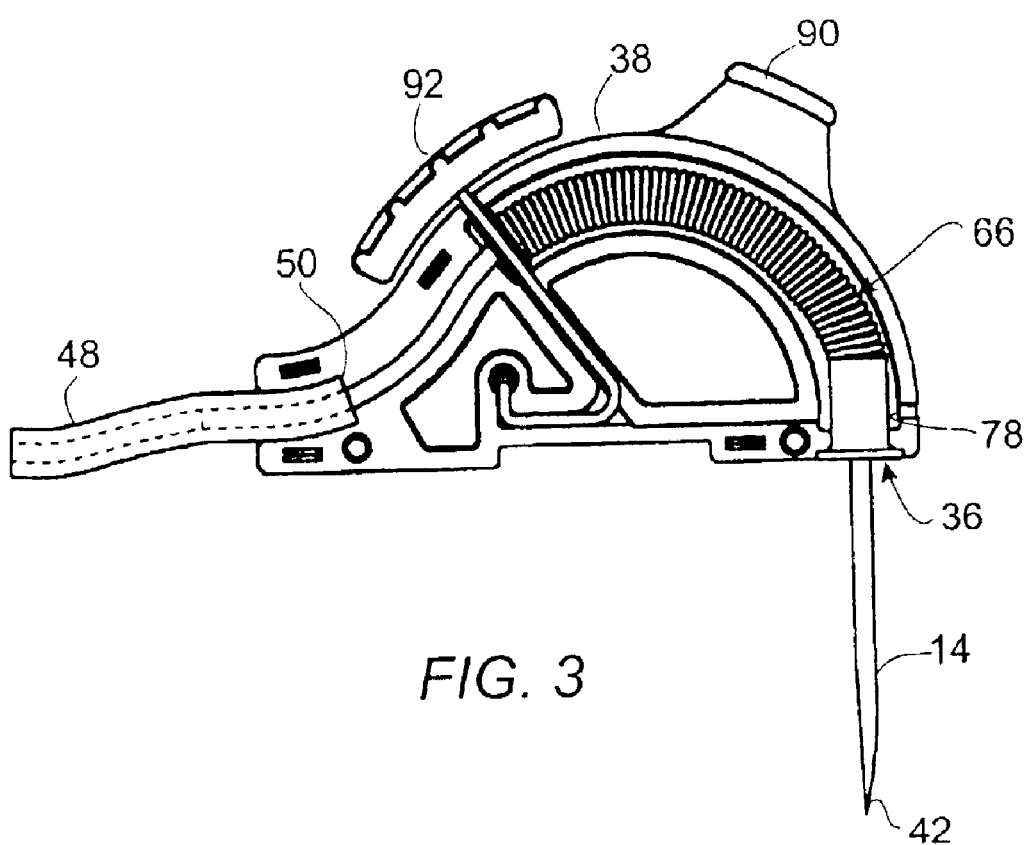
FIG. 3 is a side cross-sectional view of the safety needle device of FIG. 1 illustrating the manner in which a sheath assembly is retracted within its needle housing.
Figure 5A:
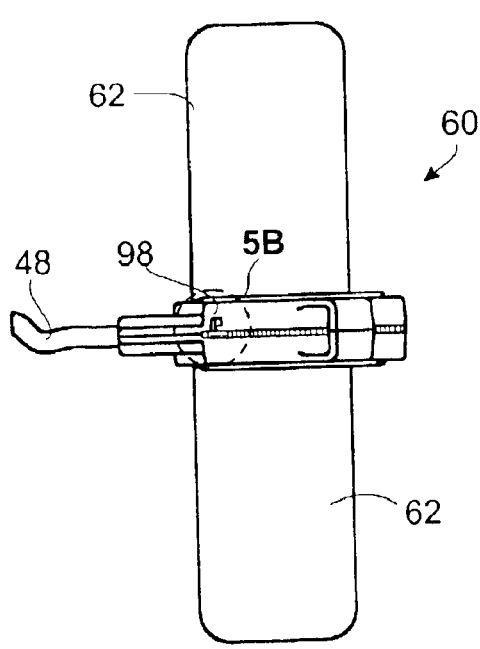
FIG. 5a is a top view of the safety needle device of FIG. 1 illustrating the flexible infusion tubing which is connected through a proximal opening of its needle housing.
Figure 5B:
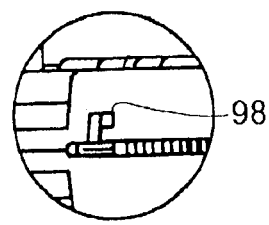
FIG. 5b is an enlarged view of the encircled portion of FIG. 5a, illustrating a proximal notch which is used for retaining a sheath assembly in a retracted position.
Figure 6B:
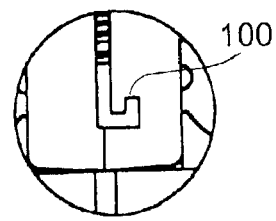
FIG. 6b is an enlarged view of the encircled portion of FIG. 6a, illustrating a distal notch which is used for securing a sheath assembly in an extended position.

FIGS. 2 and 3 show a proximal needle portion 44 of the needle 16. The proximal needle portion 44 is exposed outside of the needle housing 19 by extending through a proximal opening 46 thereof. This needle portion 44 is connected to a flexible infusion tube or tubing 48, in one end 50 of which is rigidly connected to the needle housing 18 through its proximal opening 46. The other end (not shown) of the infusion tubing is typically placed in communication with a conventional syringe or an infusion pump (not shown).

Referring specifically to FIGS. 9a and 9b, needle-retaining projections 52 are preferably formed adjacent the proximal opening 46. These projections 52 provide an interference and mechanical lock on the tubing 48 when the two housing halves 20, 22 are assembled. Moreover, the portion of the needle 16 which lies between the groove 34 and the proximal opening 46 may be secured in place through the use of a fitting track 54 or adhesive.

Figures 7A, 7B:
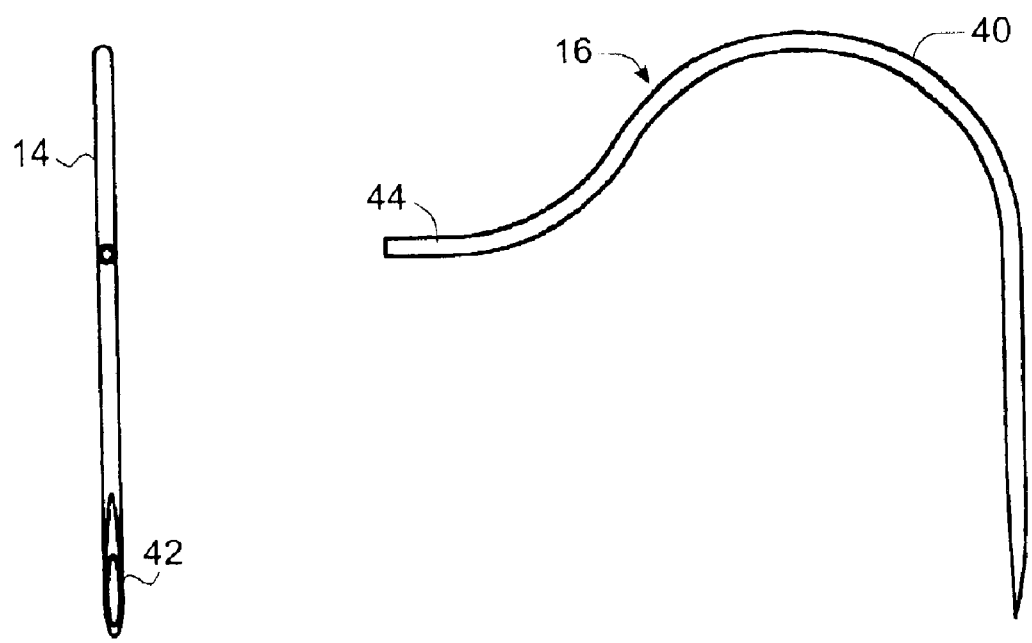
FIG. 7a is a side view of a needle having a bent intermediate portion which corresponds to the configuration of an elongate groove formed within the needle housing of FIG. 1.
FIG. 7b is a partial side view of the needle of FIG. 7a and illustrating its distal portion which defines a non-coring pointed end.

As shown in FIGS. 3 and 7a–7b, a distal needle portion 14 is provided generally opposite to the proximal needle portion 44. The distal needle portion 14 is exposed outside of the needle housing 18 extending downwardly through the distal housing opening 36. As briefly mentioned above, this portion 14 forms a needle point 42 at its exposed end which is used for penetrating the patient's skin and accessing the implanted subcutaneous IV port.

Referring now to FIGS. 1, 2, 6a and 11, the needle housing 18 has a lower housing surface 56 which defines a recess 58 underneath. This lower housing recess 58 is utilized for accommodating a hold-down platform 60. More specifically, the hold-down platform 60 is maintained within the recess 58 by various conventional attachment means (i.e., adhesive, fasteners, or the like).

The hold-down platform 60 features at least two platform strips 62 which radially extend out from the needle housing 18. In this respect, the platform strips 62 are disposed in a manner as to form a generally perpendicular relationship with the distal needle portion 14. The hold-down platform 60 is primarily used to secure the safety needle device 10 upon the patient while infusion takes place by means of taping over the platform strips 62 and the patient's skin. The platform 60 may be fabricated from any rigid or semi-rigid material such as plastic or rubber. In one configuration, the hold-down platform 60 is formed having a generally circular configuration (best shown in FIG. 11). In the other configurations, it is formed having a generally rectangular configuration (best shown in FIG. 1).

FIGS. 2, 3 and 10–12 depict an elongate sheath assembly 64 and illustrates its ability to move from within to and out of the needle housing 18. In particular, the elongate sheath assembly 64 is disposed in a retracted position designated by the numeral 66 within the internal groove 34 of the needle housing 18 in a manner as to surround the intermediate needle portion 40. The assembly 64 has a longitudinal length that is substantially equal or somewhat longer than the arcuate length of the internal groove 34. Obviously, the sheath assembly 64 has a diameter which is less than that of the groove 34 so as to allow its axial movement therewithin. Although the sheath assembly 64 may be formed from various materials, it is preferably made from an elongated wound wire constructed of stainless steel (as shown in FIG. 10).

The sheath assembly 64 includes a distal end 68 which mounts to a distal tip component 70. Preferably, the distal tip component 70 is fabricated from a plastic, preferably transparent, material. However, the distal tip component 70 should in no way be limited to such construction as other forms of rigid or semi-rigid tips (e.g., metal or rubber tips) may be used in lieu thereof. The distal tip component 70 is attached to the distal sheath end 68 either through the process of insert molding or adhesive. The tip component 70 may include a distal tip 72 having a diameter size generally greater than that of the groove's distal opening 78, but substantially equal to or lesser than the diameter of the distal housing opening 36 (as shown in FIG. 3). Alternatively, the diameter of the distal tip 72 may be sized to be somewhat similar to the diameter of the distal groove opening 78 (as shown in FIG. 11).

The sheath assembly 64 further includes a proximal sheath end 74 which is located generally opposite to the distal sheath end 68. A proximal tip component 76 is attached to the proximal sheath end 74. Similar to the distal tip component 70, the proximal tip component 76 can be attached via insert molding or adhesive. The tip component 76 has a diameter size which is generally greater than the diameter of the groove's distal opening 78. Such diameter size of the proximal tip component 76 facilitates stopping the sheath assembly 64 once it has reached its fully extended position designated generally by the numeral 80 (i.e., the distal tip component 70 being advanced over and beyond the distal needle point 42 while enclosing the distal needle portion 14 with the sheath assembly 64). Although other types of tip components may be used, the proximal tip component 76 is preferably fabricated as a stainless steel or plastic ferrule.

Referring now to FIGS. 2, 3, 8*a*–8*c* and 12, the needle housing 18 includes a biasing member 82 therewithin. This biasing member 82 is secured in place within its allocated track 84 which prevents it from bending. A blind hole 86 is also provided as a further insurance in securing the biasing member 82. Cored-out pockets 88 are defined about the biasing member 82 in order to maintain a constant wall thickness. A top projection 90 is also provided on each of the housing halves 20, 22 to resist squeezing the track 84 together and to prevent the free movement of the biasing member 82 when removing the needle 16 from the patient. The biasing member 82 is used for moving the sheath assembly 64 along the groove 34 between the retracted and extended positions 66, 80. This can be accomplished through its engagement to the proximal tip component 76 and to an outwardly exposed knob member 92.

The knob member 92 is provided external to the needle housing 18 and allows the user to manually and actively control the movement of the sheath assembly 64 along the elongated internal groove 34.

More specifically, an extension 94 of the biasing member 82 is connected to a recess 96 (shown in FIG. 10) formed on the proximal tip component 76. The biasing member's extension 94 forms a circular bend portion 95 which extends around the proximal tip component's recess 96. The extension 94 further extends out and attaches to the knob member 92 via insert molding or adhesive. Due to the torsional spring property of biasing member 82 which naturally urges the sheath assembly 64 toward the extended position 80, the user may utilize the knob member 92 to control the sheath assembly 64 when moving from its retracted to extended position.

Figure 8B:
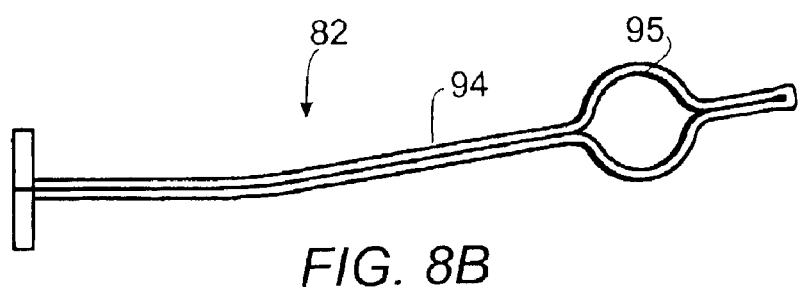
FIG. 8b is a top view of the torsional arm of FIG. 8a and illustrating the direction in which it bends when being inserted within proximal and distal notches of the needle housing.
Figure 8A:
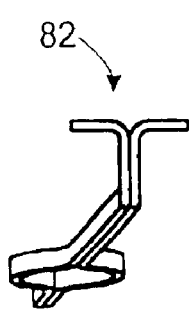
FIG. 8a is a front perspective view of a torsional arm which is used for moving the sheath assembly of FIGS. 2 and 3 between the retracted and extended positions.
Figure 8C:
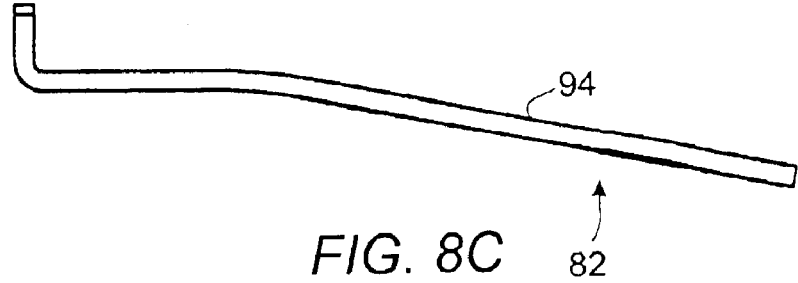
FIG. 8c is a side view of the torsional arm of FIG. 8a illustrating the direction in which it bends when the sheath assembly is moved between the retracted and extended positions.

The biasing member 82 is preferably fabricated from a resilient material such as stainless spring steel or Nitinol. Due to such elastic nature, the extension 94 of the biasing member 82 is capable of bending vertically when the sheath assembly 64 is moved between the retracted and extended positions 66, 80 (best shown in FIG. 8*c*). As illustrated in FIG. 8*b*, it can even bend sideways when the extension 94 is snapped into the proximal notch 98 (for maintaining the retracted position 66) or into the distal notch 100 (for maintaining the extended position 80). The biasing member 82 used with the present safety needle device 10 can take the form of a torsional arm or a torsional spring.

With the structure defined, the operation of the present safety needle device 10 to protect a user from getting stuck when withdrawing the needle 16 from the patient can be described. Initially, a user grabs the exterior of the housing having the distal needle point extending downwardly therefrom. The distal needle point 42 is then inserted into a designated skin area of the patient to access the implanted IV port. By such penetration, various tasks such as delivering fluids and medications, drawing blood for diagnostic testing and/or infusing blood products may be conducted. Optionally, the safety needle device 10 of the present invention can be secured in place by taping its radially extending platform strips 62 to the patient's surrounding skin area.

After performing any one of the tasks as described above, the needle 16 is withdrawn from the patient. While withdrawing the needle 16, the externally disposed knob member 92 is manipulated by the user to manually control the outward deployment of the sheath assembly 64 from its retracted position 66 to its extended position 68. Such movement is further facilitated by the torsion spring 82. When the sheath travels to its extended position 68, the sheath surrounds and covers the distal needle portion and needle tip thereby preventing any inadvertent needle stick to the user.

The safety needle device 10 of the present invention is then ready for proper disposal. Preferably, the used safety needle device 10 is thrown away in a Sharps container which is designated for used medical devices.

Additional modifications and improvements of the present invention may also be apparent to those of ordinary skill in the art. Thus, the particular combination of parts described and illustrated herein is intended to represent only certain embodiments of the present invention, and is not intended to serve as limitations of alternative devices within the spirit and scope of the invention.

What is claimed is:

1. A safety needle device for protecting a user against a needle-stick injury, the needle device comprising:
    a needle housing having a distal housing opening and a proximal housing opening;
    a groove elongated within the needle housing and communicating with the distal housing opening;
    a needle disposed within the groove and having a distal needle portion and a proximal needle portion, the distal needle portion extending away from the needle housing through the distal housing opening, and the proximal needle portion disposed outside of the groove and extending away from the needle housing through the proximal housing opening;
    an elongate sheath assembly surrounding the needle within the groove; and
    a biasing member disposed within the needle housing and being configured to move the sheath assembly along the groove and through the distal housing opening to enclose the distal needle portion therewith thereby protecting the user against the needle stick injury.

2. A safety needle device for protecting a user against a needle-stick injury, the needle device comprising:
    a needle housing having a distal housing opening and a proximal housing opening;
    a groove elongated within the needle housing and communicating with the distal housing opening;
    a needle disposed within the groove and having a distal needle portion and a proximal needle portion, the distal needle portion extending away from the needle housing through the distal housing opening, and the proximal needle portion disposed outside of the groove and extending away from the needle housing through the proximal housing opening;
    an elongate sheath assembly surrounding the needle within the groove;
    a biasing member disposed within the needle housing and being configured to move the sheath assembly along the groove and through the distal housing opening to enclose the distal needle portion therewith thereby protecting the user against the needle stick injury; and
    a flexible tubing surrounding the proximal needle portion and connecting to the needle housing through the proximal housing opening.

* * * * *